United States Patent [19]

Ronge et al.

[11] Patent Number: 5,587,519
[45] Date of Patent: Dec. 24, 1996

[54] PROCESS AND DEVICE FOR SUPPLYING GAS TO AN ANALYZER OF TRACES OF IMPURITIES IN A GAS

[75] Inventors: Catherine Ronge, Paris; Alain Mail, Draveil; Yves Marot, Buc, all of France

[73] Assignee: L'Air Liquide, Societe Anonyme pour l'Etude et l'Exploitation des Procedes Georges Claude, Paris, France

[21] Appl. No.: 370,294

[22] Filed: Jan. 9, 1995

[30] Foreign Application Priority Data

Jan. 7, 1994 [FR] France .................................. 94 00120

[51] Int. Cl.$^6$ .............................................. G01N 33/00
[52] U.S. Cl. .......................................... 73/1 G; 73/31.03
[58] Field of Search ................................ 73/1 G, 31.03; 137/1, 597, 599, 599.1, 602, 896, 897, 605, 606, 861

[56] References Cited

U.S. PATENT DOCUMENTS

| | | |
|---|---|---|
| 3,776,023 | 12/1973 | Budd et al. . |
| 3,856,033 | 12/1974 | Strain et al. .................... 137/3 |
| 3,948,281 | 4/1976 | Strain et al. .................... 137/3 |
| 4,254,797 | 3/1981 | Mayeaux ...................... 73/1 G X |
| 4,498,496 | 2/1985 | Barcellona et al. ............ 73/1 G X |
| 5,054,309 | 10/1991 | Mettes et al. .................. 73/1 G |
| 5,239,856 | 8/1993 | Mettes et al. .................. 73/1 G |
| 5,259,233 | 11/1993 | Brandt ......................... 73/1 G |
| 5,261,452 | 11/1993 | McAndrew et al. ............. 137/606 |
| 5,305,630 | 4/1994 | Molozay et al. ................ 73/1 G |

FOREIGN PATENT DOCUMENTS

| | | |
|---|---|---|
| 479633 | 4/1992 | European Pat. Off. . |
| 528386 | 2/1993 | European Pat. Off. . |
| 2219373 | 9/1974 | France . |
| 2667397 | 10/1992 | France . |
| 1385067 | 3/1988 | U.S.S.R. ...................... 73/1 G |

OTHER PUBLICATIONS

*Patent Abstracts of Japan* ABS Grp C081 vol. 5, No. 188 Abs Pub. date Nov. 27, 1981 (56–111033) "Gas Mixer".

Primary Examiner—Thomas P. Noland
Attorney, Agent, or Firm—Burns, Doane, Swecker & Mathis, L.L.P.

[57] ABSTRACT

A novel process for supplying a gas to an analyzer for measuring traces of impurities in the gas is provided. The process includes the steps of supplying the analyzer with: (i) a gas to be analyzed; (ii) a pure gas; and (iii) a standardizing gas obtained by dilution of one or more impurities in the pure gas as follows: (A) dividing a flow of pure gas into a set of at least first and second bypass lines, arranged in parallel, each of the bypass lines having an entry including a calibrated restriction, the flow of pure gas into the set of bypass lines being regulated by a flow regulator placed upstream of the set, (B) charging the pure gas of the first bypass line with a predetermined quantity of at least one impurity to obtain, after dilution with the pure gas of the second bypass line, a flow of the standardizing gas, which is directed from an exit of the set of bypass lines towards the analyzer along a feed line.

7 Claims, 1 Drawing Sheet

PROCESS AND DEVICE FOR SUPPLYING GAS TO AN ANALYZER OF TRACES OF IMPURITIES IN A GAS

BACKGROUND OF THE INVENTION (i) Field of the Invention

The present invention relates to a process and to a device for supplying gas to an analyzer of traces of impurities in a gas and, more particularly, to such a process and to such a device, according to which the analyzer is supplied sequentially with a gas to be analyzed, a pure gas and a standardizing gas obtained by dilution of one or more impurities in this pure gas.

(ii) Description of the Related Art

Such a process and such a device, designed for feeding an analyzer of very high sensitivity are known from document FR-A-2 667 397 in the Applicant's name. Such an analyzer can be designed to detect impurities in very low concentrations (for example $10^{-2}$–$10^{-5}$ ppm). It must then be frequently standardized by supplying a pure or "zero" gas and a "standardizing" gas containing impurities in accurately determined concentrations.

In the device of the abovementioned document a constant gas flow is ensured in each of the lines supplying to the analyzer the gas to be analyzed, a pure gas and a standardizing gas charged with a predetermined quantity of impurities, respectively, by arranging in each line a calibrated orifice operating in the regime and a pressure sensor upstream of this orifice, the sensed pressure control-driving a flow regulator placed in a discharge bypass of the line, downstream of the orifice. To prevent the pressure sensor from contaminating the gas traveling in the line, the sensor is fitted in a bypass equipped with a leakage line permitting a small leakage flow in this bypass. All these precautions increase the bulk of the device as well as its complexity and its cost of manufacture. The bulkiness of the device is further burdened by the use of a bottle filled with standardizing gas. Furthermore, the accuracy of flow regulation is affected by that of the pressure measurement performed by the sensor, which itself must be corrected for temperature when the latter varies.

SUMMARY AND OBJECTS OF THE INVENTION

The aim of the present invention is therefore to provide a process and a device of the type described above, which are designed so as to permit a more compact embodiment of the device, while ensuring a more accurate adjustability of the gas flows to be supplied to the analyzer.

Another aim of the present invention is to provide such a process and such a device which are guaranteed against any contamination of the gases provided by members such as pressure sensors and pressure or flow regulators, and enabling the gas for standardizing the analyzer to be changed rapidly and conveniently.

These aims of the invention, as well as others which will appear on reading the description which is to follow, are achieved with a process for supplying gas to an analyzer of traces of impurities in a gas, according to which the analyzer is supplied sequentially with a) a gas to be analyzed, b) a pure gas and c) a standardizing gas obtained by dilution of one or more impurities in this pure gas, this process being noteworthy in that a set of at least two bypass lines fitted in parallel is fed with this pure gas, the bypass pure gas of one of the lines is charged with a predetermined quantity of at least one impurity to obtain, after dilution with the bypass pure gas of the other bypass line, the standardizing gas which is directed toward the analyzer along a feed line and the flow of pure gas allowed to enter the set is divided with the aid of two calibrated restrictions, each placed at the entry of the bypass lines. The flow rate of pure gas feeding the set is regulated with the aid of a flow regulator placed upstream of the set.

As will be seen later, the use of calibrated restrictions in lines connected in parallel, in combination with a regulation of the flow feeding the bypass, makes it possible to constitute compact and accurate means of flow division, without pressure or temperature measurement, and without it being necessary to use the stages and means of calculation, traditionally associated with these measurements.

The calibrated restriction may consist of any means making it possible to carry out this division, regardless of whether it is, for example, an orifice, a capillary or a sinter.

In order to make use of the process according to the invention a device is employed including a) a source of pure gas, b) a set of at least two bypass gas lines fitted in parallel and led by the source of pure gas, c) means for charging the bypass pure gas traveling in one of the two lines with a predetermined quantity of at least one impurity, d) a restriction placed at the entry of each of the bypass lines and calibrated to divide between these two lines, in a predetermined ratio, the flow of pure gas feeding the set and e) a flow regulator of pure gas feeding the set, situated between the source of pure gas and the gas entry of the set, and in the case of each bypass line the portion of the line between the gas entry of the set and the calibrated restriction is devoid of any pressure-measuring member.

In accordance with a characteristic of the device according to the invention, the latter additionally includes two flow regulators, each placed in a discharge line connected, in the case of one, to the exit of the bypass line for gas charged with impurities and, in the case of the other, to the exit of the set.

This arrangement makes it possible to ensure an accurate adjustment of the gas flows in the two lines and of the dilution ratio of the standardizing gas charged with impurities which is delivered by one of these lines into the pure gas delivered by the other line. The device advantageously includes means allowing at least a second stage of dilution of the standardizing gas to be established.

According to one of the embodiments of the invention the device additionally includes a gas purifier placed between the source of pure gas and the gas entry of the set.

In accordance with another advantageous characteristic of the device according to the invention the means for charging with impurities the stream of bypass pure gas traveling in one of the bypass lines in parallel to form the standardizing gas consist of a plurality of permeation cartridges dispensing impurities into said line selectively or collectively, in parallel, with predetermined permeation rates. These permeation cartridges, which are particularly compact, enable the device to be reduced in bulk. The use of a complete set of such cartridges enables a standardizing gas of any predetermined composition to be produced conveniently and rapidly.

As will be clearly apparent to a person skilled in the art the process according to the invention makes it possible to perform the standardization of the analyzer by supplying it, according to the circumstances (analyzer type, user's choice), sequentially, pure gas and standardizing gas contaminated with impurity(ies) or else, for example, sequentially, two different standardizing mixtures containing different contents of impurity(ies).

Other characteristics and advantages of the present invention will become apparent on reading the description which is to follow and examining the attached drawings.

DETAILED DESCRIPTION OF PREFERRED EMBODIMENTS

Figure 1:
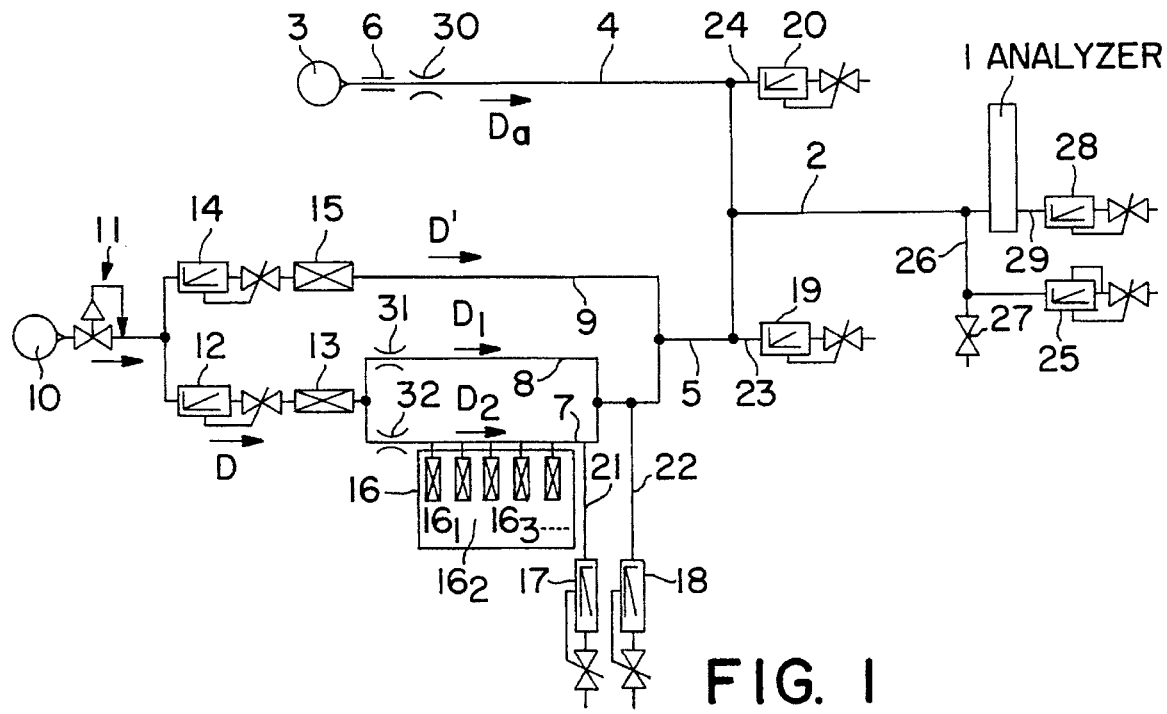
FIG. 1 shows diagrammatically the circuitry and various members of a first embodiment of the device according to the invention.

Reference is made to FIG. 1, in which a first embodiment of the device in accordance with the invention has been shown, designed for supplying gas to an analyzer 1 of very high sensitivity, capable of measuring traces of impurities present in concentrations in the range of, for example, $10^{-2}$–$10^{-5}$ ppm. This device must thus be capable of ensuring 1) the generation of a reference pure gas or "zero gas", that is to say in fact of a purified gas containing less than $10^{-5}$ ppm of impurities. 2) the generation of a standardizing gas containing traces of gases or impurities, for example $H_2O$, $CO_2$, CO, $O_2$, $CH_4$, $H_2$, and the like, in variable concentrations in a range extending from $10^{-5}$ ppm to $10^{-2}$ ppm, and 3) the control of parameters for introducing gas into the analyzer, such as pressure and flow-rate.

To do this, the device shown in FIG. 1 includes a feed line 2 of the analyzer 1, which can be selectively connected to a source 3 of a gas to be analyzed by means of a coupling line 4, or to a line 5 dispensing either a standardizing gas or a pure gas, as required for standardizing the analyzer, as is well known. This line 5 is itself fed by first, second and third lines 7, 8, 9 respectively, which are fed by a second source of gas 10, which may, furthermore, consist of the source 3 itself. The source 10 is connected to the three lines 7, 8, 9 via a pressure regulator 11, the exit of the pressure regulator being connected, on the one hand, to the set of the bypass lines 7, 8 which are fitted in parallel, via a flow regulator 12 and a purifier 13 and, on the other hand, to the additional line 9 via a flow regulator 14 and a purifier 15. Means 16, which will be described in greater detail in what follows, are provided for charging the gas stream flowing through the line 7 with impurities consisting of traces of gases such as, for example, CO, $CH_4$, $O_2$, $CO_2$ or $H_2O$.

Flow regulators 17, 18, 19, 20 are fitted in discharge lines 21, 22, 23, 24 respectively, of the line 7, of the exit of the lines 7 and 8, of the line 5 and of the line 4, respectively.

The control of the parameters for introducing gas into the analyzer 1 is ensured with the aid of an upstream pressure regulator 25 fitted as a bypass in a discharge line 26 of the line 2, this discharge line additionally including a purge valve 27, and with the aid of a flow regulator 28 fitted at the gas exit 29 from the analyzer.

Finally, the flow rate of gas in the line 4 can be adjusted and measured, conventionally, with the aid of a calibrated orifice 30 upstream of which is placed a noncontaminating pressure sensor such as an in-line piezoelectric sensor 6, for example of the "through tube" type.

It is essential that the gas flow rates $D_1$, $D_2$ in the lines 8 and 7 respectively should be set accurately, since the dilution ratio of the impurities injected by the means 16 at the exit of these lines depends on these flow rates. In accordance with an essential characteristic of the present invention this result is obtained with the aid of calibrated restrictions; in the case of the embodiment shown, of simple calibrated orifices 31, 32 fitted at the entry of the bypass lines 7, 8 respectively and of the flow regulator 12 (if appropriate with the aid of additional regulators 17 and 18), associated therewith.

Operation in a sonic regime will be given preference for the calibrated orifices of the system, but the process and device according to the invention have shown satisfactory and comparable results even when departing somewhat from the particular regime consisting of the sonic regime.

In sonic flow of gas through the orifices 31 and 32, that is to say when with each orifice the ratio of the upstream pressure to the downstream pressure is higher than 2, it is known that the mass flow rates $D_1$ and $D_2$ of the gas in these orifices 32, 31 respectively are equal to:

$$D_1 = K_{GAS} \times P \times T^{-1/2} \times S_1 = \alpha \times P \times S_1$$

$$D_2 = K_{GAS} \times P \times T^{-1/2} \times S_2 = \alpha \times P \times S_2$$

with $D = D_1 + D_2$, being the total flow rate of the gas supplied to lines 7 and 8, P = pressure upstream of the orifices T = temperature, which is common to both orifices if they are close to each other, $K_{GAS}$ = constant which depends only on the nature of the gas and on the geometry of the orifice, these geometries being assumed to be identical (for example circular) for both orifices 31 and 32, $S_1$, $S_2$ = sections of the orifices 31, 32 respectively.

The above relationships give:

$$D_1 = D \times S_1 / (S_1 + S_2)$$

$$D_2 = D \times S_2 / (S_1 + S_2)$$

It will be noted that, for a given total flow rate D, the accuracy $\Delta D_i / D_i$ for each of the flow rates depends on the accuracy reached in the ratio of the sections $S_1$ and $S_2$, that is, in the case of $D_1$:

$$\Delta D_1 / D_1 = \Delta(S_2/S_1)/(1 + S_2/S_1)$$

The pressure P upstream of the orifices is automatically balanced to the value:

$$P = D / (\alpha \times (S_1 + S_2))$$

In order that the orifices 31 and 32 may be employed in a sonic regime in the range of the flow rates D in question, the sum of the sections $S_1 + S_2$ of these orifices must be such as to give, for each orifice:

$$P/P_{DOWNSTREAM} > 2$$

where $P_{DOWNSTREAM}$ is the pressure downstream of the orifice in question.

Thus, advantageously, the flow division thus obtained does not require any pressure measurement or temperature measurement, favouring the compactness, the simplicity and the cost of manufacture of the device in accordance with the invention. The division principle thus established can be generalized to a set of N calibrated orifices, as will be seen later in connection with FIG. 2.

In the case of conditions departing slightly from the sonic regime (pressure ratio equal to 2 or slightly less than 2), the flow delivered to the set is nevertheless distributed in the ratio of the areas of the calibrated orifices (or else in the ratio of the pressure drops introduced by a capillary or a sinter).

Nevertheless, the more the conditions depart from such a ratio 2, the more sensitive will the system be to variations in downstream pressure, With regard to the regulation and the control of the flows in the various lines of the device in accordance with the invention, it will be noted that all the components capable of contaminating the gas, for example at a level of $10^{-5}$ ppm or more, such as a valve or a flow regulator, have been systematically placed either upstream of the purifiers (flow regulators 12, 14, pressure regulators 11) or bypassing or downstream of the critical lines (flow regulators 17, 18, 19, 20, 25).

Returning to the means 16 employed for charging the gas traveling in the line 7 with traces of gases or impurities, and for diluting the gas thus charged so as to obtain "standard" gases of accurately determined composition, according to the invention, these means advantageously consist of a battery of permeation cartridges ($16_1$, $16_2$, $16_3$, and so on) charged with gases such as $O_2$, $CO_2$, $H_2O$, $CH_4$, $CO$, $H_2$ and the like. These cartridges may be fitted in parallel in the lane 7, to dispense continuously and simultaneously into the latter, or else to be separately connected to the line 7 via simple two- or three-way valves, which may be considered to be noncontaminating at the high impurity concentrations of the gas in the lane 7, before dilution in the gas delivered by the lanes 8 and 9. These cartridges are commonly small in bulk (for example 2×2×10 cm) and can therefore remain fitted permanently in the device, occupying little space. When cartridges whose permeation rate τ is small are chosen the lifetime of such a cartridge can then be longer than 1 year.

The concentration C of impurities introduced by a cartridge $16_1$ with a permeation rate τ in the gas of flow rate $D_2$ flowing in the lane 7 is:

$$C = K\tau/D_2$$

τ depending on the nature of a permeation membrane with which the cartridge is equipped, of the gas and of the temperature, K being the constant for the gas in question.

It will be understood that the introduction of a battery 16 of permeation cartridges $16_1$ into the device in accordance with the invention provides the latter with greater compactness and a long lifetime, and offers a wide choice of the gases which can be introduced to form the gases for standardizing the analyzer. These standardizing gases are obtained after dilution of the gas leaving the line 7 in the pure gas of flow rate $D_1$ leaving the line 8, and then the dilution of the resulting ting gas in the pure gas of flow rate D' leaving the lane 9, these dilutions being controlled by the flow regulators 17, 18.

In accordance with an advantageous characteristic of the device according to the invention, all the lines of the device are continually purged with gas, so as to maintain the internal surfaces of the lines in dynamic absorption/desorption equilibrium, to avoid transient regimes in respect of pressure/flow rate, during which any surface in contact with the gas is capable of desorbing and of adsorbing molecules, a process that is liable to modify the composition of the gases which are formed.

In accordance with yet another advantageous characteristic of the device according to the invention, all the exits of the mass flow regulators and those of the purge line 27 are combined and assembled into a single exit (not shown) directed, for example, toward a purifier, before discharge or optional recycling. Any modification of the composition of the gases which are formed, due to possible back-diffusion of gas through obese exits is thus prevented. In addition, it is then possible to employ flammable or toxic gases which require special precautions.

The operation of the device according to the invention will now be explained, firstly in a stage of analysis of a gas of flow rate $D_a$ originating from the source 3, secondly in a stage of standardization of the analyzer with the aid of a "zero" gas and of standardizing gas.

In an analysis stage it is obviously necessary that the lines 21, 22 and 5 should absorb completely the gases dispensed by the lines 7, 8 and 9 in order that these gases should not enter the analyzer feed line 2. The flow rates $D_{ij}$ which are set by the regulators ij in question must then satisfy the relationship:

$$D_{19}+D_{17}+D_{18}>D_{12}+D_{14}$$

That is $(D_{19}+D_{17}+D_{18})-(D_{12}+D_{14})=R>0$.

The excess flow rate R must then originate from the line 4.

If the leakage flow rate in the line 24 is also set at R (in order to maintain a gas flow therein), the flow rate of gas $D_{28}$ in the analyzer satisfies the relationship:

$$D_{28}<D_a-2R$$

The discrepancy from equality being due to the leakage flow rate in the pressure regulator 25 and to possible losses in the analyzer.

In a particular embodiment of the device in accordance with the invention, in which the flow rates $D_1$, $D_2$ in the lines 8 and 7 respectively are equal and established with the aid of circular sonic orifices 31, 2 calibrated at 62 μm, where the maximum flow rates of the regulators 12, 14, 17, 18, 19, 20 and 24 are 190 cc/min, 5 l/min, 100 cc/min, 7 l/min, 10 l/min and 5 l/min respectively, R=200 cc/min was chosen.

In order to send a pure or "zero" standardizing gas into the analyzer 1 it is necessary to short-circuit the flow $D_a$ from the line 4 into the leakage line 24 and that from the line 7 into the line 21. With the flow-rate regulation parameters shown above it is then possible to choose:

$$D_{14}=5 \text{ l/min}$$

$$D_{12}=190 \text{ cc/min}=D$$

$$D_{17}=D_{18}=100 \text{ cc/min}$$

$$D_{19}=R$$

$$D_{20}=D_A+R$$

R=200 cc/min, for example

In order to send into the analyzer 1 only the standardizing gas formed in the line 7 it is necessary to short-circuit the flow $D_a$ as shown above and to regulate the dilution of the impurities in the gas supplied by the source 10 by an appropriate adjustment of the flow rates in the lines 21 and 22, by virtue of the flow regulator 17 and 18 respectively, that is, for example:

$$D_{14}=5 \text{ l/min}$$

$$D_{12}=190 \text{ cc/min}=D$$

$$D_{19}=R$$

$$D_{17}<D_2$$

$$D_{18}<D-D_{17}$$

$$D_{20}=D_A+R$$

The concentration C of the standardizing gas or mixture supplied to the analyzer is of the form:

$$C=C_0 \times Q_1 \times Q_2$$

where $C_0=K\tau/D_2$ as already seen, and $Q_1$, $Q_2$ are the dilution factors of the first and second dilution stages respectively, which can be adjusted with the aid of the flow radiators 17 and 18 respectively, it being possible for the product $Q_1 \times Q_2$ then to take any value, for example between $5 \times 10^{-5}$ and $2 \times 10^{-2}$.

With a pure gas consisting of oxygen and a permeation cartridge of permeation rate $\tau=50$ ng/min it has thus been possible to form standard mixtures with contents of between $1.8 \times 10^{-5}$ ppm and $7.5 \times 10^{-3}$ ppm.

Thus it appears that the dilution of the impurities in the standardizing gas and the switching of the three types of gas to be supplied to the analyzer can be obtained merely by control-driving the various flow regulators of the device according to the invention. The latter therefore lends itself to an automation in which the adjustment of these radiators could be ensured, for example, by a computer duly programmed for this purpose.

Figure 2:
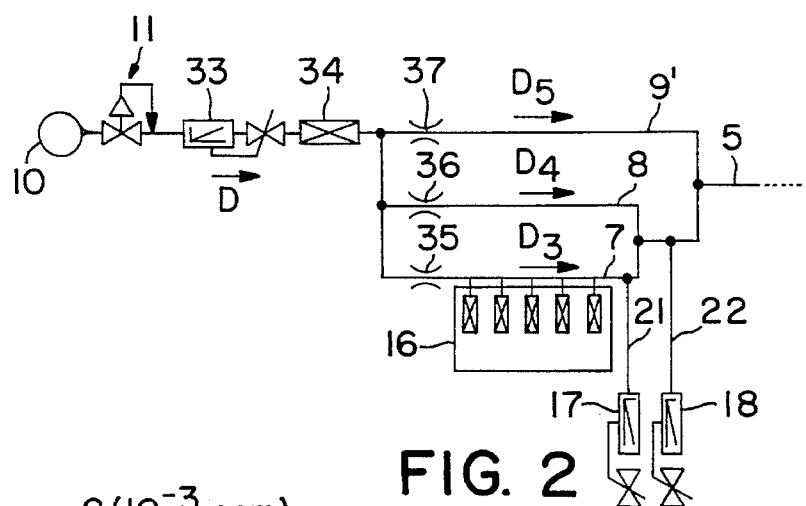
FIG. 2 shows diagrammatically an alternative form of a part of the device of FIG. 1.

FIG. 2 shows an alternative fore (7, 8, 9') of the arrangement of the lines 7, 8, 9 of FIG. 1 and of the associated regulators and purifiers. In this arrangement a single flow regulator 33 and a single purifier 34 are employed for feeding the three lines, the additional line 9' being connected between the common entry of the lines 7 and 8 and the common exit of these lines. The flow rates $D_3$, $D_4$, $D_5$ in the lines 7, 8, 9' are then set by calibrated sonic orifices 35, 36, 37 respectively, of sections $S_3$, $S_4$, $S_5$ respectively, of diameter $d_3$, $d_4$, $d_5$, in accordance with the relationships:

$$D_3=D \times S_3/(S_3+S_4+S_5)$$

$$D_4=D \times S_4/(S_3+S_4+S_5)$$

$$D_5=D \times S_5/(S_3+S_4+S_5)$$

With $d_3=d_4=60$ μm and $d_5=400$ μm, for example, the performance of the device of FIG. 1 is found again with:

$$D_3=D_4=95 \text{ cc/min}$$

$$D_5=5000 \text{ cc/min}$$

to the benefit of lesser bulkiness, complexity and cost of manufacture of the device, as a result of the elimination of one regulator and one purifier.

Figure 3:
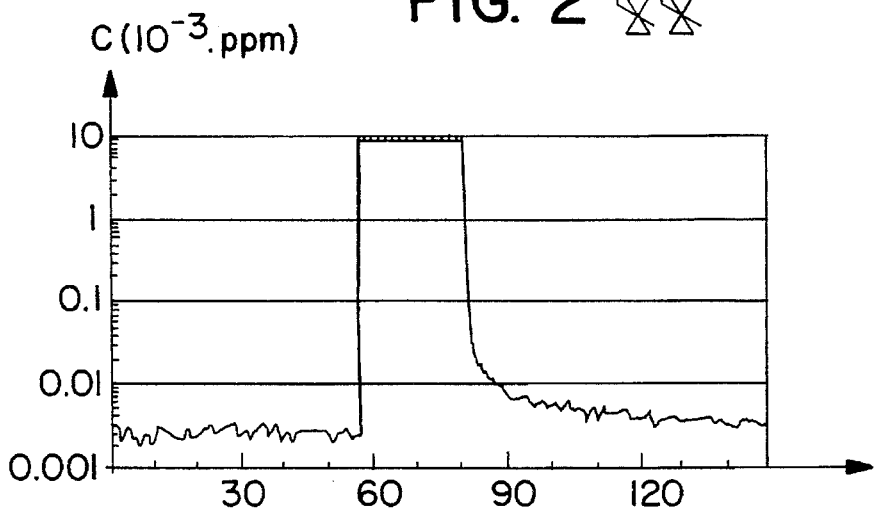
FIG. 3 is a graph representing the change in the impurity concentration of a standardizing gas when the latter is formed with the aid of the device according to the invention.

The device in accordance with the invention can be used in combination, for example, with an analysis apparatus consisting of an ionization mass spectrometer at atmospheric pressure, in order to supply it, inter alia, with a zero gas containing less than $2 \times 10^{-6}$ ppm of oxygen and less than $10^{-5}$ ppm of water. FIG. 3 gives the graph provided by such a spectrometer when its feed is switched between a zero gas and a mixture containing 0.009 ppm of oxygen, the graph showing that this switching takes place substantially instantaneously.

It now appears that the invention makes it possible to achieve the set objectives, namely to produce a device for supplying gas to an analyzer, which is at the same time accurate, simple in design and small in bulk, especially as a result of the elimination of any pressure sampling upstream of the restrictions, and other stages of calculation which were associated therewith, quick to use and purge, exhibiting a very short response time when the concentration of impurities is changed during the standardization, enabling the standardizing gas to be changed simply and rapidly by virtue of the battery of permeation cartridges which is employed, and which is easy to automate.

The invention is obviously not restricted to the embodiments described and shown, which have been given merely by way of example. Thus, it would not constitute a departure from the present invention to increase the number of lines fitted between the source 10 and the line 5, in order to increase the number of dilution stages of the standardizing gas beyond the two stages which are seen in FIGS. 1 and 2.

We claim:

1. A process for supplying a gas to an analyzer for measuring traces of impurities in the gas comprising supplying said analyzer with
   (i) a gas to be analyzed;
   (ii) a pure gas; and
   (iii) a standardizing gas obtained by dilution of one or more impurities in said pure gas as follows:
      (A) dividing a flow of pure gas into a set of at least first and second bypass lines, arranged in parallel, each of said bypass lines having an entry including a calibrated restriction, the flow rate of pure gas fed into said set of bypass lines being regulated by a flow regulator placed upstream of the set,
      (B) charging the pure gas of the first bypass line with a predetermined quantity of at least one impurity to obtain, after dilution with the pure gas of the second bypass line, a flow of the standardizing gas, which is directed from an exit of said set of bypass lines towards the analyzer along a feed line, wherein the gas to be analyzed, the pure gas, and the standardizing gas flow continuously.

2. The process as claimed in claim 1, further comprising regulating the flow of the standardizing gas obtained at the exit of the set of bypass lines with:
   (i) a first flow regulator placed in a discharge line connected to an exit of the first bypass line for gas charged with impurities upstream of the gas exit of the set of bypass lines; and (ii) a second flow regulator placed in a discharge line connected to the gas exit of the set of bypass lines.

3. The process as claimed in claim 1, further comprising the step of subjecting the standardizing gas, on leaving the set of bypass lines and before reaching the analyzer, to another dilution stage by the introduction of an additional quantity of pure gas.

4. The process as claimed in claim 1, wherein said calibrated restriction is a calibrated orifice.

5. The process as claimed in claim 4, wherein said calibrated orifice is employed in a sonic regime.

6. The process as claimed in claim 1, wherein the impurities are generated by one or more permeation cartridges.

7. The process as claimed in claim 1, further comprising maintaining internal surfaces of all lines in dynamic absorption/desorption equilibrium.

* * * * *